(12) United States Patent
Raugel

(10) Patent No.: US 6,972,021 B2
(45) Date of Patent: Dec. 6, 2005

(54) HANDLING DEVICE FOR ACETABULAR BEARING LINER

(75) Inventor: Patrick Raugel, Amboise (FR)

(73) Assignee: Benoist Girard SAS, (FR)

( * ) Notice: Subject to any disclaimer, the term of this patent is extended or adjusted under 35 U.S.C. 154(b) by 423 days.

(21) Appl. No.: 10/007,130

(22) Filed: Nov. 5, 2001

(65) Prior Publication Data

US 2002/0082706 A1 Jun. 27, 2002

(30) Foreign Application Priority Data

Nov. 7, 2000 (GB) .................................. 0027206

(51) Int. Cl.$^7$ ............................................... A61F 2/34
(52) U.S. Cl. ........................................................ 606/91
(58) Field of Search ..................... 606/110–115, 200, 606/153, 149, 152, 100; 623/22.11, 22.29, 623/22.24–22.28; 220/375, 839, 836, 837; 215/306

(56) References Cited

U.S. PATENT DOCUMENTS

| | | | | |
|---|---|---|---|---|
| 3,924,738 A | * | 12/1975 | Poupitch | ..................... 206/150 |
| 4,974,735 A | * | 12/1990 | Newell et al. | ............... 215/253 |
| 5,163,691 A | * | 11/1992 | Lederman | ................... 277/551 |
| D353,328 S | * | 12/1994 | Nuffer | .......................... D9/446 |
| 5,413,603 A | | 5/1995 | Noiles et al. | |
| 5,431,657 A | | 7/1995 | Rohr | |
| 6,302,286 B1 | * | 10/2001 | Witherspoon | .............. 215/11.6 |
| 6,451,058 B2 | * | 9/2002 | Tuke et al. | ............... 623/22.21 |

FOREIGN PATENT DOCUMENTS

| | | |
|---|---|---|
| DE | 198 20 721 A1 | 4/1999 |
| DE | 299 22 792 U1 | 4/2000 |
| EP | 0 636 351 | 1/1995 |
| FR | 2 789 570 | 12/1999 |

* cited by examiner

Primary Examiner—Anhtuan T. Nguyen
Assistant Examiner—D. Jacob Davis
(74) Attorney, Agent, or Firm—Lerner, David, Littenberg, Krumholz & Mentlik, LLP

(57) ABSTRACT

A handling device to hold a bearing liner which is to be introduced into the socket of an acetabular cup has a support provided with an alignment element on the acetabular cup and having an opening which has a deformable rim adapted to receive the outer circumference of the bearing liner to be inserted. The bearing liner which may be, for example, conically tapered, is inserted into the opening in the support until the rim on the handling device is engaged. The held bearing liner can now be accurately located in a tapered socket of the acetabular cup utilizing the alignment device. Because the lower surface of the support rests against the upper rim of the acetabular cup, the complementary tapered bearing surfaces are not fully engaged. Engagement is achieved by pushing the bearing liner downwards through the deformable rim of the opening in the support so that the liner is correctly inserted. The handling device is now free of the bearing liner and can be removed.

10 Claims, 2 Drawing Sheets

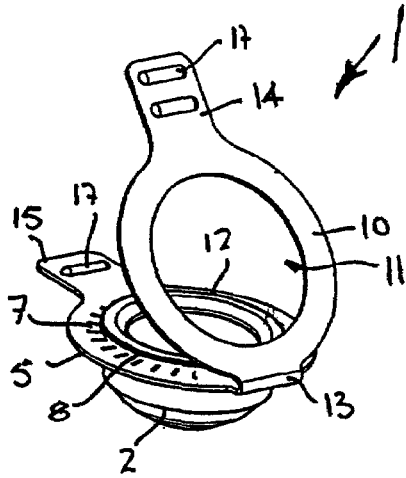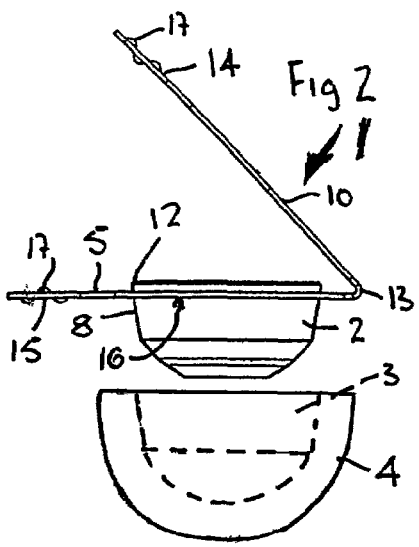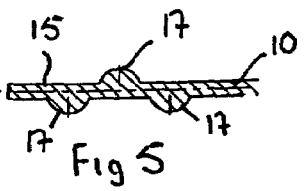

HANDLING DEVICE FOR ACETABULAR BEARING LINER

BACKGROUND OF THE INVENTION

This invention relates to a handling device for use with a bearing liner which is to be introduced into the socket of a prosthetic acetabular cup.

Acetabular cups are often provided with a bearing liner and such a liner can be made from a ceramic material. Bearing liners of this type are relatively fragile but in some constructions the liner is adapted to be held in the socket by the provision of a taper on the outside wall of the liner engaging a corresponding taper on the inner wall of the socket.

U.S. Pat. No. 5,413,603 shows a socket bearing which has a male taper adapted to self-lock into a cup provided with an appropriate co-operating female taper.

Because of the relatively fragile nature of ceramic liners great care must be taken to ensure that the tapers are in alignment and it is quite easy to misalign the tapers and wedge the liner out of alignment. This can create difficulties in removing the liner especially if the socket has already been implanted in the acetabulum.

A further difficulty is that if excess pressure is applied onto a misaligned ceramic bearing liner it is capable of cracking the ceramic liner. It is also possible to chip and damage such ceramic liners and every precaution must be taken to avoid this. The present invention is intended to overcome some of the difficulties referred to above.

SUMMARY OF THE INVENTION

According to the present invention a handling device to hold a bearing liner which is to be introduced into the socket of an acetabular cup comprises a support provided with an alignment element on the acetabular cup and having an opening which has a deformable rim around the perimeter of the opening adapted to receive the outer circumference of the bearing liner to be inserted. The deformable rim may be in the form of a plurality of resiliently deformable elements which are deformed by and thereby hold the bearing liner in place.

Thus, a bearing liner, for example of the tapered type, is inserted into the opening in the support until the rim is engaged. The held bearing liner can now be accurately located in the tapered socket utilizing the alignment element. Because the lower surface of the support rests against the upper rim of the acetabular cup, the bearing liner is not fully engaged. This is easily achieved by pushing the bearing liner downwards through the deformable rim of the opening in the support so that the liner is correctly inserted. The handling device is now free of the bearing liner and can be removed.

Preferably the alignment element on the acetabular cup is formed by a substantially flat lower surface surrounding the opening. The support can be in the form of a substantially flat plate and can be made from a sheet material, for example a synthetic plastics material. The perimeter of the opening in the support can have a castellated rim which thus assists the rim to deform when the bearing liner is pushed through it.

The device can also include an element for retaining the bearing liner in the opening in the support and this retainer can, for example, be provided by the deformable rim itself which is adapted to resiliently grip the bearing liner.

In another embodiment the retainer can be provided by a retainer adapted to extend across the upper rim of the bearing liner and securing elements can be provided for securing the retainer to the support, for example by clips or studs.

Alternatively the retainer can be formed by an extended portion of the support which is bent back across the upper rim of the bearing liner.

In one preferred embodiment the retainer is provided with an opening of smaller dimensions than the upper outer rim of the bearing liner, the opening being aligned with the opening in the support when in use.

In an alternative construction the retainer can be formed with a manually deformable portion which is aligned with the opening in the support when in use. With this arrangement the deformable portion is deformed by pushing it inwards to detach the bearing liner from the support.

If desired an operating handle can be included which is adapted to manually deform the deformable portion to allow the handle to bear on the cup portion of the bearing liner to displace it from the support.

A device can be provided to allow the operating handle to pass through a reception opening in the retainer so that it can bear against the surface of the cup portion of the bearing liner but cannot be withdrawn without carrying the retainer with it.

In this arrangement the reception opening can be provided with a screw thread through which a cooperating screw thread on the operating handle can pass.

The invention also includes a handling device as set forth above which is located on a bearing liner and is incorporated in a sterile package.

Thus, the bearing liner can be held sterile in the package, the bearing liner lifted out of the package by the handling device and used by the surgeon without further sterilization.

BRIEF DESCRIPTION OF THE DRAWINGS

The invention can be performed in various ways and some embodiments will now be described by way of example and with reference to the accompanying drawings in which:

FIG. 1 is an isometric view of a device according to the invention in place on a bearing liner ready for insertion into a socket;

FIG. 2 is a side elevation of the device shown in FIG. 1;

FIG. 3 is a plan view of the device shown in FIG. 2;

FIG. 4 is a plan view of the device shown in FIG. 1 in its opened position;

FIG. 5 is an enlarged cross-sectional side elevation of part of the device shown in FIGS. 1 to 4;

FIG. 6 is a side elevation of a device according to the invention located on a bearing liner and incorporated in a sterile package;

DETAILED DESCRIPTION

Figure 7:
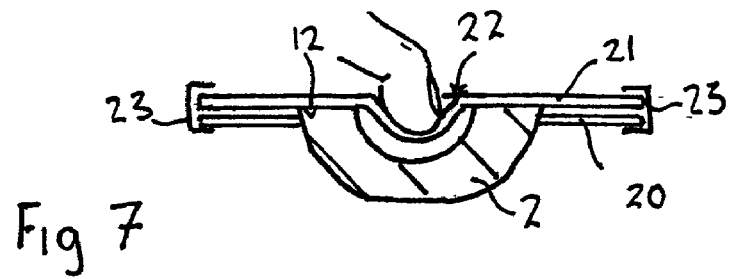
FIG. 7 is a diagrammatic part cross-sectional side elevation of another construction according to the invention.

In a first preferred embodiment of the invention and as shown in FIGS. 1 to 6 a handling device according to present invention generally denoted as 1 for holding a bearing liner 2 which is to be introduced into a socket 3 of an acetabular cup 4 (FIG. 2) comprises a support in the form of a first portion 5 which is provided with an opening 6 which has a radially incised deformable rim 7. The bearing liner 2 may be made of ceramic and have a tapered outer surface designed to lockingly engage a complementary tapered inner surface in socket 3. Incisions or slits 9 extend around the circumference of rim 7 and extend radially outwardly to a diameter slightly larger than the largest outer diameter of bearing liner 2. The incisions 9 could be replaced by slots or castellations to provide the deformable rim. Opening 6 is adapted to receive the outer circumference 8 of bearing liner 2. This outer circumference 8 is tapered so that the bearing liner sits in opening 6 with its upper rim projecting in the manner shown in FIGS. 1 and 2. The relative diameters of liner 2 and rim 7 and choice of material of first portion 5 can be such that rim 7 is adapted to resiliently grip liner 2. The handling device also includes a retainer provided by a second portion 10 which has an opening 11 which is of smaller diameter than the upper outer circumference 12 of bearing liner 2.

In the preferred embodiment, second portion 10 forms an extension of first portion 5 and they are hinged together at 13 by any suitable hinge construction. In a preferred embodiment, as shown in the drawings, the first and second portions are formed as a tray hinged at its center. First portion 5 has a projecting handle 14 which is repeated in second portion 10 by a handle 15.

The first and second portions may conveniently be made from sheet material, for example a synthetic plastics material such as PETG copolyester film made by LUSTRO and about 0.7 mm thick. The thickness of the material required will depend upon the characteristics of the material used. The lower surface 16 of first portion 5 is substantially flat when it is in position, as shown in FIG. 1 to act as means for alignment on acetabular cup 4. Due to the resilience of the thin sheet material however second portion 10 can be bent over the upper rim of the bearing liner so that the handles 14 and 15 are closely adjacent, as shown in FIG. 6, and this assists in maneuvering the device when in use and retains the bearing liner in place.

In order to assist handling of the device bosses 17 are provided on the handles 14 and 15 as it is most clearly shown in FIG. 5.

FIG. 6 shows how the handle device can be located on a bearing liner which has been incorporated into and sealed within a sterile package. The same reference numerals are used to indicate similar parts to those used in FIGS. 1 to 5 and it will be seen that second portion 10 has been moved down so that it can now lie flat against the upper rim 12 of the bearing liner. The bearing liner and handling device are encapsulated in the well-known form of a bubble package which usually incorporate a DuPont TYVEK® protective backing 18 which has been encapsulated by a blown thermoplastics material bubble 19.

The handling device and bearing liner can therefore be maintained in a sterile condition and only removed by the surgeon when they are required. With this arrangement it is only necessary for the surgeon to move first portion 5 until it engages the rim 12 of the bearing liner, fold the second portion down to the position shown in FIG. 6 and use the liner to correctly locate and insert the bearing liner into socket 3 of acetabular cup 4. The surgeon now releases the second portion, opens it away from the first portion and pushes bearing liner 2 through deformable rim 7 into place in the socket 3 correctly engaging the tapered walls due tot the fact that he can place lower surface 16 of first portion 5 directly on the upper rim of the acetabular cup he knows that it will be substantially correctly aligned due to its flat lower surface. With the bearing liner in place the handling device is removed from the area.

FIG. 7 shows an alternative embodiment in which the bearing liner is again indicated by reference numeral 2. In this embodiment the support 20 again has an opening and edge as described with regard to the embodiment shown in FIGS. 1 to 6 but the retainer 21 not only extends across the upper rim 12 of the bearing liner 2 but is formed at its center portion above the bearing liner socket with a manually deformable portion 22 which is aligned with the opening in the support 20. The deformable portion can be formed by a series of radially extending slots or incisions (not shown) or by treating this portion, for example by localized heating, to render it easily deformable. In the construction shown in FIG. 7 clips 23 are provided at each end for securing the retainer 21 to the support 20. The bearing liner is aligned in a similar manner to that described with regard to FIGS. 1 to 6 but is simply pushed into place by the surgeon's finger, the manually deformable portion 22 deforming appropriately to allow the bearing liner to be detached from the support 20.

Figure 8:
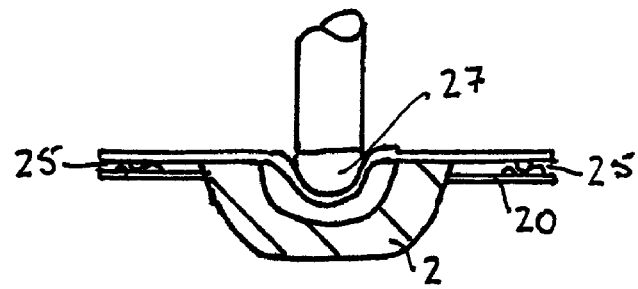
FIG. 8 is a diagrammatic cross-sectional side elevation of another alternative construction.
Figure 9:
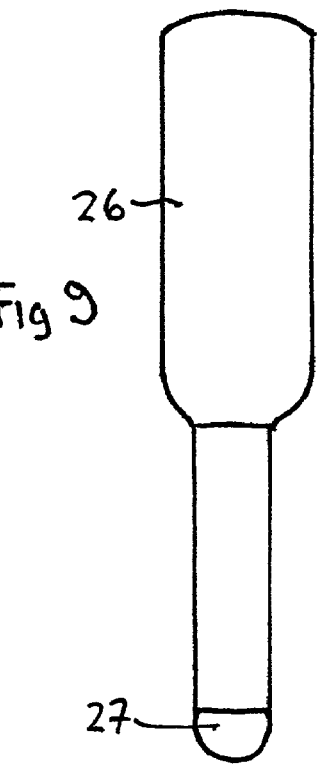
FIG. 9 is a diagrammatic illustration of an operating handle for use with the construction shown in FIG. 8.

FIG. 8 shows a somewhat similar embodiment to that shown in FIG. 7 but in this arrangement the clips 23 are dispensed with and molded snap fasteners 25 are provided to hold the retainer and the support together. This figure shows how an operating handle, as shown in FIG. 9, and indicated by reference numeral 26, can be used. The operating handle has an appropriately rounded end 27 which is used in place of the surgeon's finger.

Figure 10:
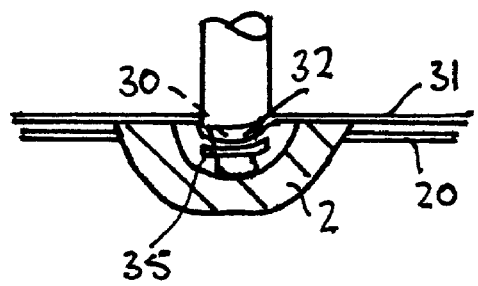
FIG. 10 is an enlarged view of another alternative construction.
Figure 11:
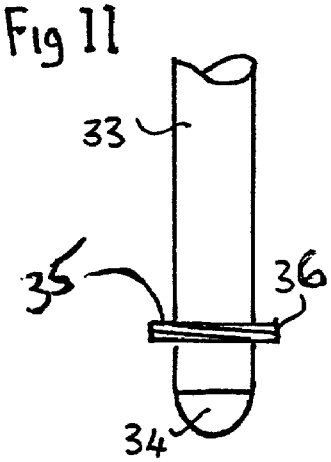
FIG. 11 shows part of an operating handle for use with the construction shown in FIG. 10.

FIG. 10 shows yet another embodiment which is rather similar to that shown in FIGS. 7 and 8 but in this arrangement a screw threaded opening 30 is provided in the retainer 31. This opening 30 is provided in a collar 32. The operating handle for use with this arrangement is indicated by reference numeral 33 in FIG. 11 and has a rounded end 34 similar to that shown in FIG. 9. Spaced away from the rounded end 34 is a flange 35 which carries a single screw thread 36. In use, the single screw thread 35 on the handle 33 is rotated through the threaded opening 30 until the threaded flange is clear of the opening, that is as shown in FIG. 10. The handle can now be pushed further down to release the bearing liner 2 from the support 20 and the handle is then used to remove the handling device completely. Thus the surgeon need not touch the equipment at all. With the flange 35 held in the screw threaded opening 30 the handling device, complete with bearing liner, can be maneuvered into place.

Figure 12:
FIG. 12 is a part cross-sectional diagrammatic side elevation of a simplified constructions according to the invention.

FIG. 12 shows a simplified embodiment in which the support 40 is again formed from a sheet of plastics material and can again have the castellated deformable edge to its central opening but with this arrangement the edge of the opening is provided with a resilient bead 41 which is adapted to resiliently grip the bearing liner. Thus, with this construction the alignment means are again provided by the lower surface of the support 40, the handling device can be positioned with the bearing liner in place and it is merely necessary to push the bearing liner through the resiliently gripping deformable rim to locate it in place in the acetabular cup.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. An instrument for aligning a liner in an outer shell of a two-piece prosthetic acetabular cup, the liner having a tapered male surface and an open end for receiving a bearing element and a shell having a complimentary tapered female surface comprising:

a support having a first portion with an opening having a perimeter for resiliently gripping the liner adjacent the open end thereof, the perimeter being in the form of a plurality of resiliently deformable elements, said support first portion including a handle portion for allowing the alignment of the tapered male surface in the liner with the tapered female surface on the shell said support having a second portion pivotally coupled to said first portion and pivotal from a position parallel to said opening to a position angled with respect to said opening.

2. The instrument as set forth in claim 1 wherein the support is made of plastic.

3. The instrument of claim 2 wherein the perimeter of the first portion surrounds an inner opening sized to receive an outer perimeter of the liner.

4. The instrument of claim 3 wherein the resiliently deformable elements are formed by slits in said plastic extending radially outwardly from said inner perimeter of said opening.

5. The instrument as set forth in claim 1 wherein said a second portion contacts said liner at the open end thereof for preventing said liner from moving out of engagement with said resilient elements upon insertion of said liner into said shell.

6. The instrument as set forth in claim 5 wherein the support is made of plastic.

7. The instrument of claim 6 wherein the perimeter of the first portion surrounds an inner opening sized to receive an outer perimeter of the liner.

8. The instrument of claim 7 wherein the resiliently deformable elements are formed by slits in said plastic extending radially outwardly from said inner perimeter of said opening.

9. The instrument as set forth in claim 5 wherein said first and second portions are connected by a hinged joint.

10. The instrument as set forth in claim 9 wherein said hinged joint forms part of said handle.

* * * * *